(12) United States Patent
Gade (10) Patent No.: US 7,927,331 B2
(45) Date of Patent: Apr. 19, 2011

(54) METHOD AND APPARATUS FOR SURGICAL POCKET CREATION AND DISSECTION

(75) Inventor: Prasad V. Gade, Newburgh, IN (US)

(73) Assignee: M15 Innovations LLC, Newburgh, IN (US)

( * ) Notice: Subject to any disclaimer, the term of this patent is extended or adjusted under 35 U.S.C. 154(b) by 1012 days.

(21) Appl. No.: 11/623,158

(22) Filed: Jan. 15, 2007

(65) Prior Publication Data

US 2008/0091188 A1 Apr. 17, 2008

Related U.S. Application Data

(60) Provisional application No. 60/759,384, filed on Jan. 17, 2006.

(51) Int. Cl.
*A61B 18/14* (2006.01)
(52) U.S. Cl. .............................. 606/45; 606/41; 607/101
(58) Field of Classification Search .................... 606/41, 606/45–46, 190; 607/101
See application file for complete search history.

(56) References Cited

U.S. PATENT DOCUMENTS

| 5,452,732 | A | 9/1995 | Bircoli |
| 5,630,813 | A | 5/1997 | Kieturakis |
| 5,655,545 | A | 8/1997 | Johnson |
| 5,897,590 | A | 4/1999 | Donovan |
| 6,440,121 | B1 * | 8/2002 | Weber et al. ............... 606/2 |
| 6,921,364 | B2 | 7/2005 | Mollenauer |
| 7,611,512 | B2 * | 11/2009 | Ein-Gal ....................... 606/50 |
| 2001/0025190 | A1 * | 9/2001 | Weber et al. ................ 607/89 |
| 2004/0006388 | A1 | 1/2004 | Rehnke |
| 2004/0049251 | A1 * | 3/2004 | Knowlton ................... 607/101 |

* cited by examiner

*Primary Examiner* — Linda C Dvorak
*Assistant Examiner* — Jaymi Della
(74) *Attorney, Agent, or Firm* — Woodard, Emhardt, Moriarty, McNett & Henry LLP (57) ABSTRACT

A surgical instrument for creation of tissue dissection and creation of space is disclosed. The instrument may be used any place in the body where a physician could or would use finger or instrument dissection to create a tissue pocket or space. The pocket dissector can be used under direct vision, laparoscopically, endoscopically, under fluoroscopic guidance or blindly.

23 Claims, 8 Drawing Sheets

METHOD AND APPARATUS FOR SURGICAL POCKET CREATION AND DISSECTION

The present application claims the benefit of provisional application Ser. No. 60/759,384, filed on Jan. 17, 2006, which application is incorporated herein by reference in its entirety.

The present disclosure relates generally to surgical dissection and creation of space within tissue, such as creating a space along the tissue planes or creating an artificial tissue plane.

Various types of implants are placed within the human body for treatment affecting various conditions or organ systems. Implantation of devices can require creation of a tissue pocket, such as may be located within the chest or abdominal wall. For the creation of a proper tissue pocket, surgical skill is required. For subcutaneous implants (a majority of implants are of this location) creation of a tissue pocket in the subcutaneous fat layer under the skin is needed in many cases, and if this pocket is too superficial or too tight the implant may erode through the skin or a skin incision may not heal. On the other hand, a relatively deep pocket makes access for the implant more challenging. The pocket needs to be a good size match for the implant. If the pocket is larger than the implant, the risk of seroma or hematoma will increase along with risk of implant infection. There is also a risk of implant inversion unless one or more anchoring sutures are placed. As mentioned above, tissue pockets which are too tight may result in skin necrosis or erosion of the implant through the skin. Another factor in implant pocket preparation is good hemostasis and control of lymphatic channels. Current methods include controlling the bleeding points with electrocautery or ligatures, which is done under suboptimal conditions because of poor visualization.

Implant pocket creation is currently being done with the help of blunt dissection, sharp dissection and control of bleeding points. However, the current methods are not very precise and sometimes the pocket is too small or too large. Currently available tools include surgical scissors, finger dissection, and various forms of energy including electrocautery, ultrasonic energy, laser energy or ligatures for control of bleeding points. These instruments have limitations as mentioned above.

A method of creating a surgical pocket with a dissection glove is shown in U.S. Pat. No. 5,897,590 to Donovan. This method uses a dissecting glove and the method of creating the pocket is similar to the conventional way of creating pocket.

Other options available include balloon dissection instruments, where a tissue pocket is created by blunt force produced by expanding balloon. This technique can sometimes provide a more precise tissue pocket but no hemostasis or lymphostasis is achieved. This method is more of use for tissue expansion than for creating surgical pockets.

An electro-cauterizing dissector and method for facilitating breast implant procedure is shown in U.S. Pat. No. 5,630,813 to Kieturakis. This method uses a balloon dissector with a cauterizing element integrated on the surface of the balloon. This method will result in nonselective cauterization of all the tissue in contact with the balloon and may increase the tissue damage.

SUMMARY

The present disclosure includes a surgical apparatus for cutting and cauterizing tissue, including a handle portion with an opening there through, and an operating portion connected to the handle portion. The operating portion includes a plurality of projections each having a respective sharpened tip and a base portion, the projections being separated from one another by respective gaps, and the operating portion having an upper surface with a ridge adjacent the projections and a mound behind the ridge. An electrical conductor can extend through the handle portion and operating portion, and a cauterization element can be connected to the conductor, extending through base portions of the projections and exposed in said gaps, so that the tips of the projections are forward of the cauterization element. The operating portion can be of a size and shape that is substantially the same as an implant, and the cauterization element can be electrically connected to the conductor. The tips can form a convex leading edge for sharp dissection. In certain embodiments, the operating portion includes a bay for holding an implant, with the bay having internal walls sized to be at least as tall as the implant. The operating portion can be detachable from the handle portion and biocompatible so that the operating portion may be included as part of an implant, with the operating portion having at least one channel for anchoring one or more sutures. The operating portion can be narrow and planar, with the projections forming one side of it, and/or the operating portion may be elastic and have an unstressed shape. A sheath can be provided through which the handle portion extends, wherein the operating portion is retractable into and extendable from the sheath, and when extended from the sheath, the operating portion assumes the unstressed shape.

Methods are also disclosed, which may include providing a unitary apparatus that is capable of sharp dissection, blunt dissection and cauterization at the same time, having a set of projections with sharp tips for sharp dissection, upper and lower surfaces for blunt dissection, and a cauterization element extending between said projections for cauterization; making an incision into a patient; and inserting at least a portion of said apparatus into the patient through the incision. Such methods can also include creating a subcutaneous pocket for an implant with the apparatus, which may be of a size closely matching that of the implant by virtue of an operating portion of the apparatus having a size and shape substantially the same as the implant, and placing an implant in the pocket. A skin flap could be created in the patient, and an implant device could be placed under the skin flap. Tissue can be excised from the patient using the apparatus. In certain embodiments, the incision is made by the apparatus. If the apparatus includes an operating portion having a bay configured to accommodate an implant, methods can include placing an implant in the bay, and the inserting can included inserting the implant located in the bay into the patient. Where such an apparatus includes a handle portion detachably connected to the operating portion, a method can include detaching the handle portion from the operating portion, for example after the insertion.

DESCRIPTION OF THE ILLUSTRATED EMBODIMENTS

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated device, and such further applications of the principles of the disclosure as illustrated therein, being contemplated as would normally occur to one skilled in the art to which the disclosure relates.

Referring generally to the figures, there is shown an embodiment of an instrument 20 that is able to combine various types of tissue dissection methods to facilitate precise entry into and through tissue with minimal tissue damage. Instrument 20 preferably includes the ability to perform cautery at substantially the same time, thus limiting fluid flow, e.g. maintaining a level of hemostasis and lymphostasis. As is further discussed below, instrument 20 may be used to create an incision through skin and perhaps other tissues and to create a pocket or space for placement of an implant that is designed for the particular implant, while minimizing blood loss and trauma to the surrounding tissues. Control of and limiting fluid flow can be done relatively selectively, substantially with respect to the tissue bordering the space or pocket, as opposed to inserting a balloon or similar device.

Figure 1:
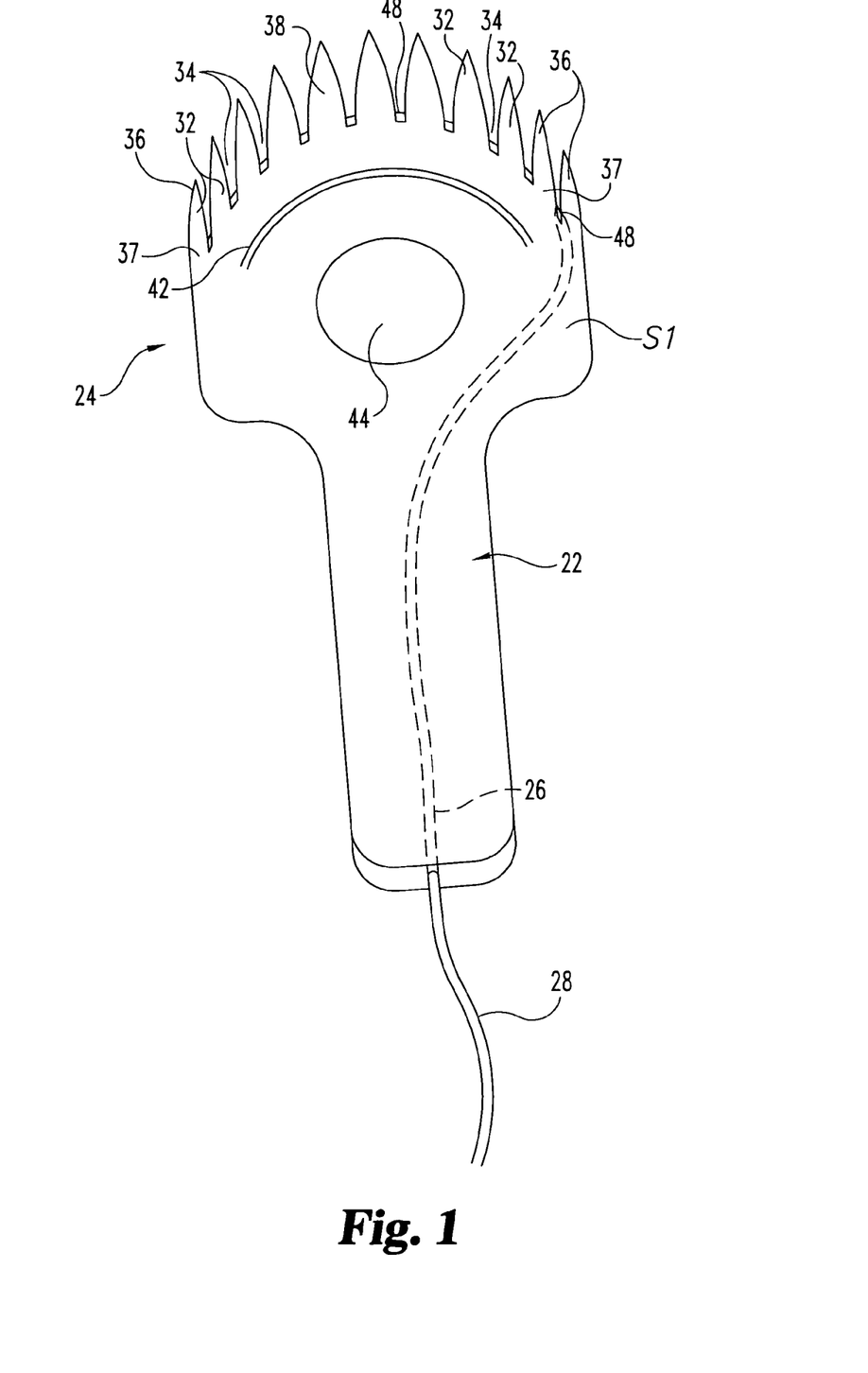
FIG. 1 is a top plan view of one embodiment of an instrument according to the present disclosure.
Figure 2:
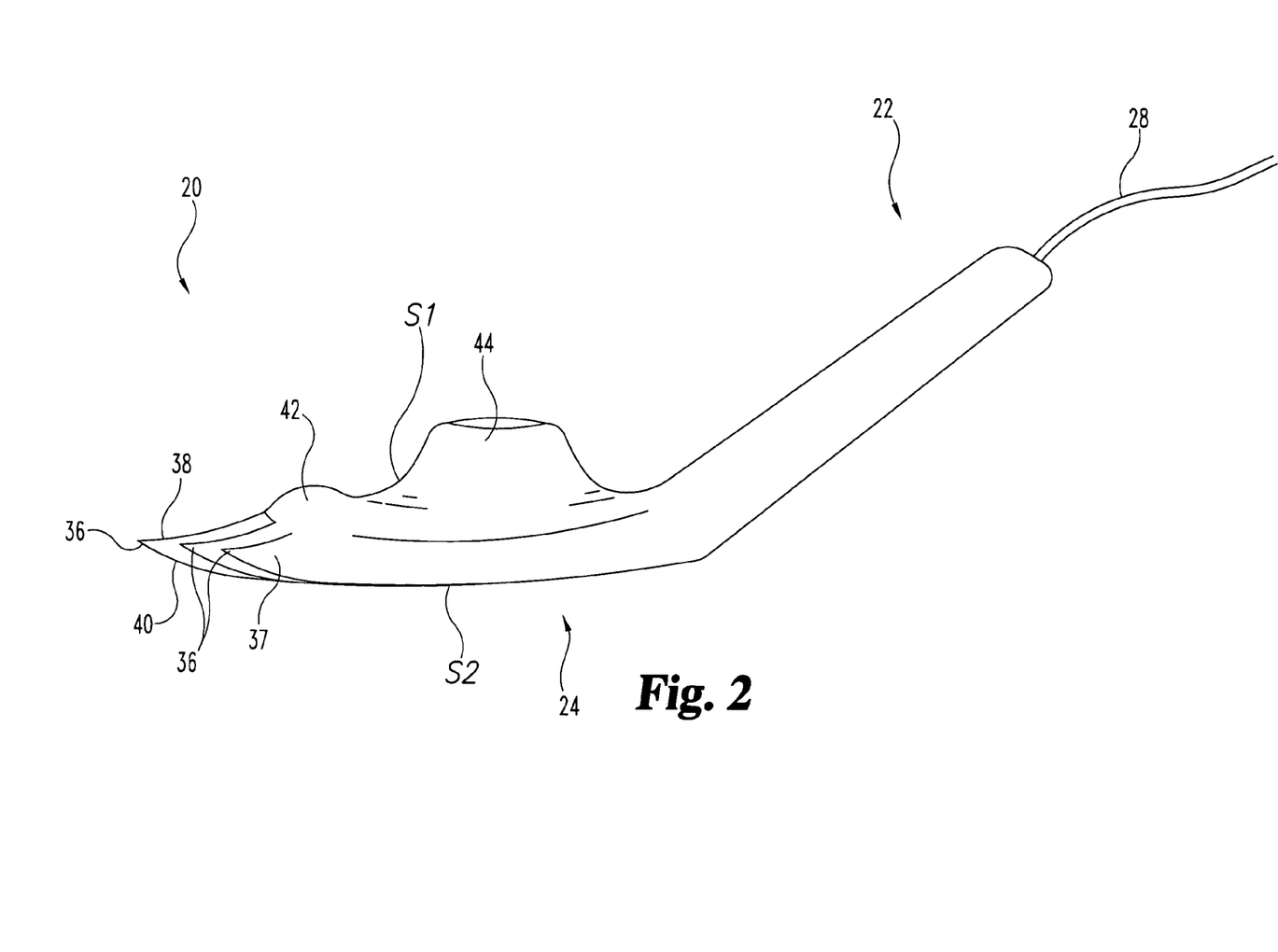
FIG. 2 is a side elevational view of the embodiment shown in FIG. 1, the view from the opposite side being a mirror image.

In the illustrated embodiment, instrument 20 includes a handle portion 22 that is integral or unitary with an operating portion 24. Handle portion 22 is elongated and sized and configured generally to fit the hand of a surgeon or other user. Thus, handle portion 22 may have the rough shape of a rectangular solid, it may be substantially cylindrical with a circular or oval cross-section, it may be curved, and/or it may have indentations for one or more of the fingers. Handle portion 22 includes an opening 26, in this particular embodiment, through which a wire or cable 28 runs. Wire or cable 28 is of a material capable of conducting electricity in this embodiment, such as copper, and is preferably insulated for the safety of the user and the patient. As seen in FIG. 1, wire 28 extends through handle 22 and into operating portion 24, and in the other direction wire 28 exits handle 22 and is connected to a source of electrical power (not shown). In this way, electrical power from the source enters this embodiment of instrument 20 through wire 28, which transmits the power to operating portion 24, as will be discussed further below. While handle 22 is shown in one rigid piece in this embodiment, it is to be understood that an articulating handle may also be employed if desired.

Operating end 24 of instrument 20, in this embodiment, includes a set of projections or teeth 32, between which are a set of gaps 34. In the illustrated embodiment, ten projections 32 are shown, including the projections at either side of instrument 20, and those projections 32 are separated by nine gaps 34. For the sake of clarity in the drawings, only selected projections 32 and gaps 34 are indicated with their respective numbers. It will be seen that operating portion 24 could include a different number of projections 32 and gaps 34, as the width of operating portion 24 and/or the desired width of projections 32 and gaps 34 may suggest. It is preferable, however, to have a set of at least two projections 32, as indicated further below.

Operating portion 24 forms a leading edge of instrument 20, and so each projection 32 in this embodiment includes a tip 36 that is sharpened for sharp dissection of tissue, and a base portion 37. Tips 36 have a sharpened edge having a width dimension in the illustrated embodiment, which edge may be straight, convexly curved, or otherwise configured. In other embodiments, tips 36 may come to a sharp point for sharp dissection. As seen in FIG. 1, a line connecting tips 36 generally describes an arc in the illustrated embodiment, and in a particular case that arc may be part of a circle. Projections 32 also generally have an upper surface 38 and a lower surface 40 extending from tips 36 toward handle 22. (As used herein, "upper" and "lower" are used with reference to the drawings simply to differentiate parts, but are not intended to convey an absolute placement of the indicated items.) Upper surfaces 38 of respective projections 32 generally meet behind gaps 34, and those united surfaces rise to form a protective ridge 42, which in the illustrated embodiment forms a part-circular arc. A rounded mound 44 is generally behind ridge 42 in this embodiment, and with ridge 42 acts to move adjacent tissues away from instrument 20 (i.e. blunt dissection) after sharp dissection by tips 36, as is further described below. Upper surfaces 38 of projections 32, ridge 42, and mound 44 may be considered part of an upper surface S1 of instrument 20 or operating portion 24. Lower surfaces 40 of projections 32 generally meet behind projections 32, and may be considered part of a lower surface S2 of instrument 20 or operating portion 24. In the illustrated embodiment, lower surface S2 has a slight convex curvature to allow some spreading of tissue and to minimize friction with adjacent tissue.

Operating end 24 further includes an cauterization element 48 that is connected to wire or cable 28. Element 48 connects to wire or cable 28 at or adjacent to a gap 34 in operating end 24, and passes through at least some of the projections 32, for example at or adjacent to base portions 37. Element 48 is exposed in gaps 34, and if desired, insulation may be provided around element 48 as it passes through projections 32. Element 48 is, in its simplest form, a heating element that heats to a temperature necessary for cauterizing blood vessels, lymphatic vessels, ligamentous structures or other tissues. The temperature may be regulated by choice of material for element 48, and also by regulation of electrical current passed to element 48 through wire 28, as by providing a known regulating device (not shown) at or downstream of the power source. In other embodiments, element 48 may use or be energized by radio-frequency (RF) energy, ultrasonic energy, or other types of deliverable energy to enable cauterization. Element 48 may be adjacent one or both of upper surfaces 38 and lower surfaces 40 of projections 32. In this way, a cauterization element 48 is provided just proximal (from the point of view of the user) of the sharp dissection tips 36 of instrument 20, so that cauterization can take place almost immediately following the tissue dissection.

The configuration of operating portion 24 is intended to follow or be substantially the same as the configuration of the implant to be inserted into the patient's body. Thus, if the item to be implanted is a pacemaker, for example, the general size and shape of operating portion 24 will approximate that of the pacemaker. As another example, if the item to be implanted is an infusion port, operating portion 24 will be generally sized and configured to approximate the port. Accordingly, for a roughly square or rectangular implant, operating portion 24 will be roughly square or rectangular (e.g. with some or all of tips 36 of projections 32 in approximately a straight line). For an implant with a convex side, a convex cutting area (as seen in one example in FIG. 1) can be used. For a cylindrical implant such as a percutaneous port, operating portion 24 can be roughly cylindrical, with tips 36 of projections 32 forming a circle or oval (e.g. around or centered on an axis through handle 22). It has been found that shaping the operating end 24 of instrument 20 according to the implant to be placed results in reduced overall trauma or damage to the tissue, and a pocket or space sized for the implant is formed with little or no other damage to neighboring tissues. As noted previously, such a pocket more closely matching the configuration of the implant can lessen the risk of complications.

Figure 3:
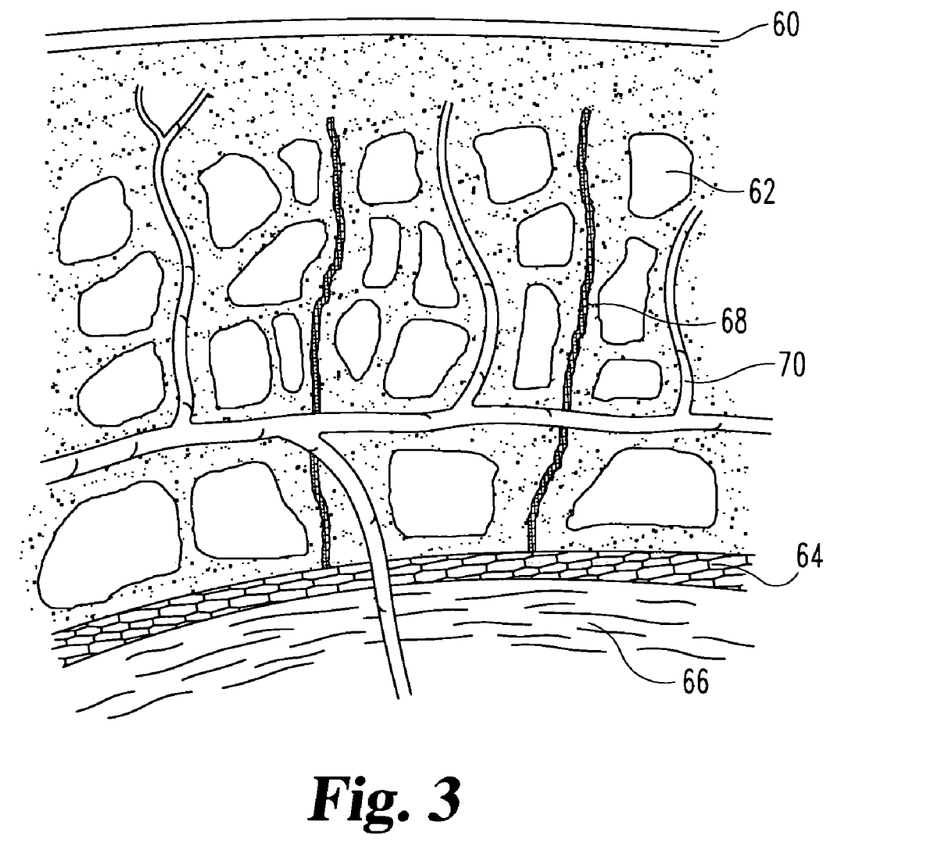
FIG. 3 is a sectional representation of human subcutaneous tissue.

The illustrated embodiment of instrument 20 can be used for sharp and blunt dissection, with cauterization, to create an opening in tissue and implant a device into the body. For the sake of illustration, the following discussion will refer to subcutaneous implantation of a pacemaker device, but as indicated above, a variety of implants may be placed in conjunction with the use of different embodiments of instrument 20. FIG. 3 depicts generally a cross-section of human tissue, with the skin layer 60 uppermost, followed by the fat layer 62, the fascia 64, and muscle tissue 66. Also indicated are lymphatic channels 68 extending generally from the fascia 64 through the fat layer 62, and small arterial blood vessels 70.

In general, for creation of a subcutaneous pocket a skin incision is made using standard methods, e.g. by way of a scalpel or other sharp objects. Tips 36 could be used for such an incision. Subsequently, tips 36 forming a leading edge or dissecting edge of instrument 20 is engaged at a select depth in the tissue to create a tissue plane and a tissue pocket. The tissue plane can be created between two tissue layers (for example, between the subcutaneous fat and fascia), or within a single tissue layer (for example, dividing and dissecting subcutaneous fat). The leading edge is used for sharp dissection, with the surfaces of instrument 20 providing blunt dissection, and the energy delivered through wire or cable 28 to cauterization element 48 at the base 37 of projections or teeth 32 is used to coagulate and divide blood vessels and lymphatic channels. Accordingly, a pocket that is a good fit for a given implant, with good hemostasis, is created in one step.

Figure 4:
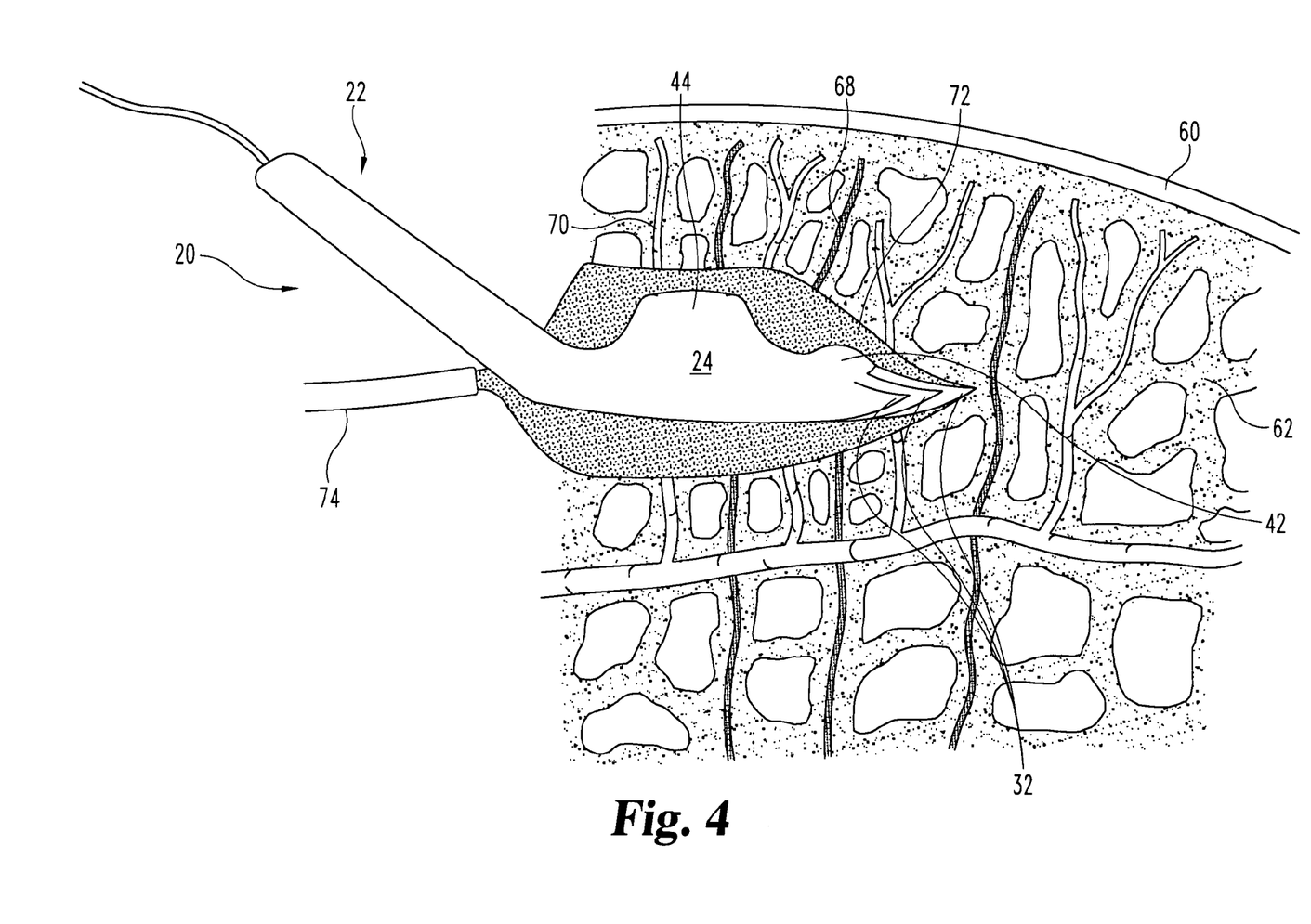
FIG. 4 is a representation of the embodiment shown in FIG. 1 inserted into human subcutaneous tissue and creating a tissue pocket.

As noted, instrument 20 may be inserted directly through the skin layer 60, with tips 36 of projections 32 providing sharp dissection to that tissue, or an initial incision may be made by another device to open the skin to the tissue layers below. Cauterization element 48 is energized, so that vessels that are cut can be cauterized as instrument 20 progresses. As indicated in FIG. 4, instrument 20 is moved through the fat layer 62 to the desired location for implantation of the pacemaker (not shown). As instrument 20 is moved, tips 36 perform sharp dissection on the tissue in front of instrument 20. The tissue (fatty tissue in this example) moves along the upper surfaces 38 and lower surfaces 40 of operating end 24, and along with ridge 42 and mound 44 they move the tissue out of the way. Thus, fatty tissue is generally kept away from the electrocautery element, resulting in less or no heat damage to that subcutaneous fat. Blood and lymphatic vessels are cut by tips 36 as instrument 20 moves forward, and their exposed surfaces are cauterized by element 48 as the vessels move along projections 32 and gaps 34. With the overall shape of operating end 24, including mound 44, being sized approximately the same as the implant to be placed, a pocket 72 is created through sharp and blunt dissection that is substantially the right size for the implant. Fluid loss is kept to a minimum by virtue of the progression of cauterization element 48 directly behind the sharp dissection. If desired, a suction device 74 may be introduced behind instrument 20 to remove additional fluids.

Following insertion of instrument 20 and creation of pocket 72, the pacemaker or other implant may be inserted into pocket 72. Instrument 20 is removed from the surgical site, and proper connection of the pacemaker or other procedures with the implant may be conducted. When the implant is situated as the surgeon desires, procedures to close the pocket and percutaneous incision can be made to conclude the surgery.

Figure 5:
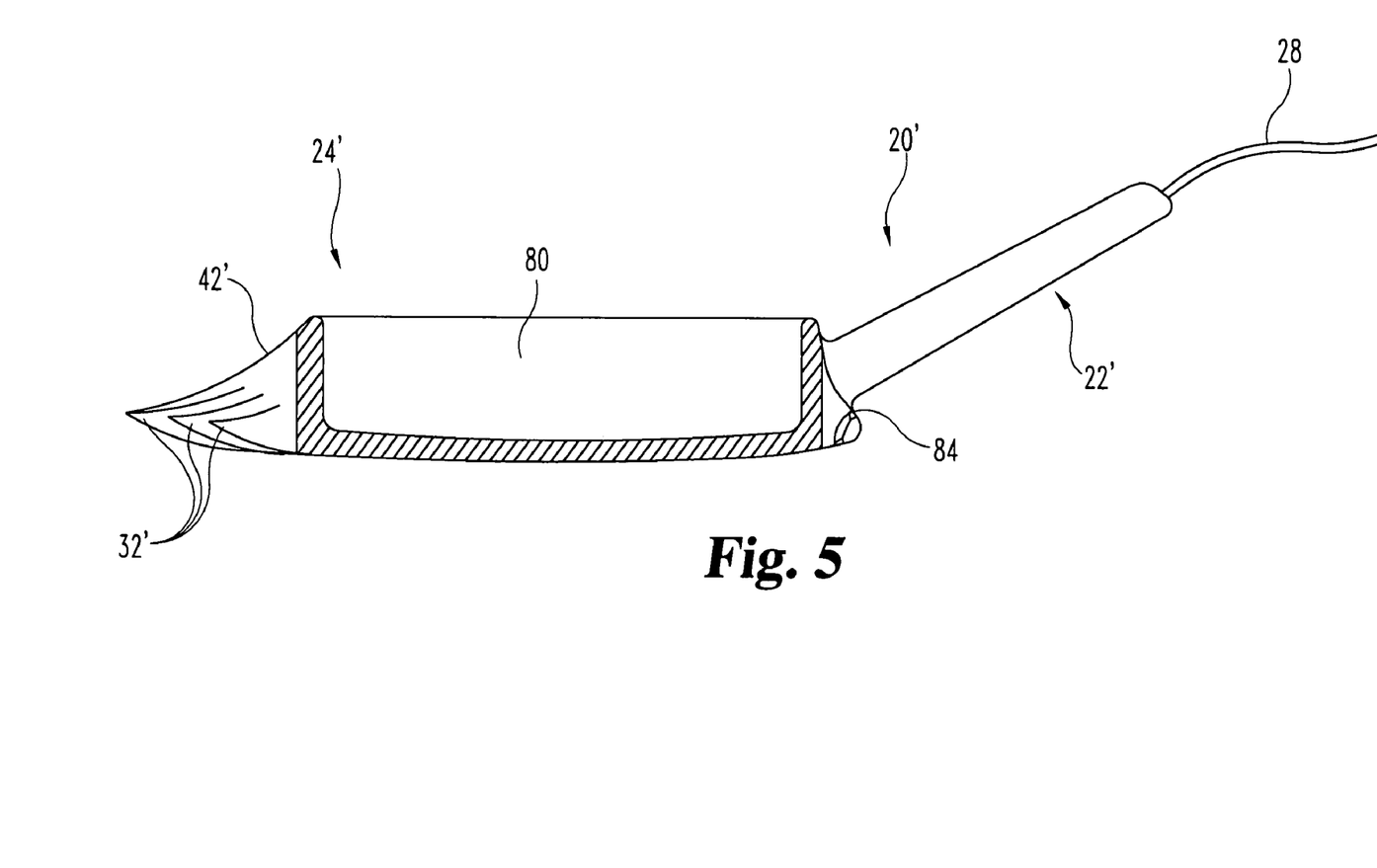
FIG. 5. is a part cross-sectional view of an embodiment of an instrument according to the present disclosure that can be used as a dissector as well as implant receiver.
Figure 5A:
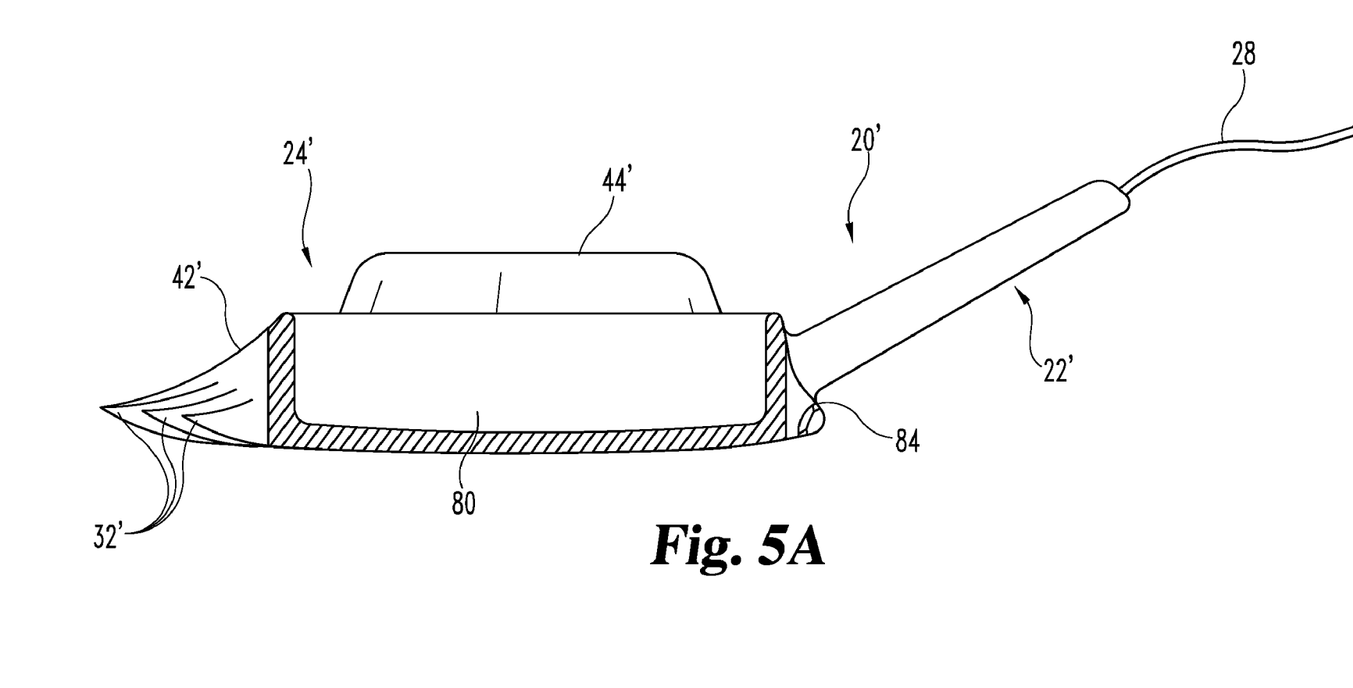
FIG. 5A is a part cross-sectional view of an embodiment of an instrument according to the present disclosure that can be used as a dissector as well as implant receiver.

Instrument 20 may also be configured to transport the implant along with creating the space for it. Referring generally to FIG. 5, an instrument 20' is shown that is identical or similar in most respects to instrument 20 described above. Thus, instrument 20' includes a handle portion 22', and an operating portion 24' having a set of projections 32', a rising ridge portion 42', and mound 44'. Operating portion 24' is substantially the same as operating portion 24, with the exception that a bay 80 is provided in operating portion 24'. Bay 80 is sized and configured to allow placement of an implant inside for transport of the implant into a pocket in a patient formed by instrument 20'. Thus, internal walls 82 may define all or part of bay 80, and preferably are as tall or taller than the height of an implant placed in bay 80. In this way, the implant is generally kept away from tissue during insertion, limiting any opportunity for the implant to damage the adjacent tissue. In a particular embodiment of instrument 20', the operating portion 24' may be made part of the implant itself, so that the implanted device need not be removed from bay 80 once it arrives at pocket 72. In that embodiment, accordingly, handle 22' connects wire or cable 28 to operating portion 24', yet is unpluggable or otherwise detachable from operating portion 24' for removal from the patient. Operating portion 24' is also provided, in that embodiment, with a channel 84 on a proximal portion for anchoring one or more sutures, to maintain operating portion 24' and the device in its bay 80 in place within pocket 72. Tips 36' can act as stabilizers for the device-and-operating-portion implant, as they remain embedded in tissue.

Use of instrument 20' is substantially the same as the use of instrument 20. As with instrument 20, instrument 20' is inserted and moved to the desired implant location, with sharp and blunt dissection and cauterization occurring along the way. At the desired location, handle 22' is detached from operating portion 24' and is removed from the patient. Anchoring sutures are placed in channel 84 and adjacent tissue, and the pocket and associated incision(s) are closed. With instrument 20', consequently, separate steps of preparing the pocket for the implant and placement of the implant are not necessary, but a single step of incision and placement is possible.

Figure 6:
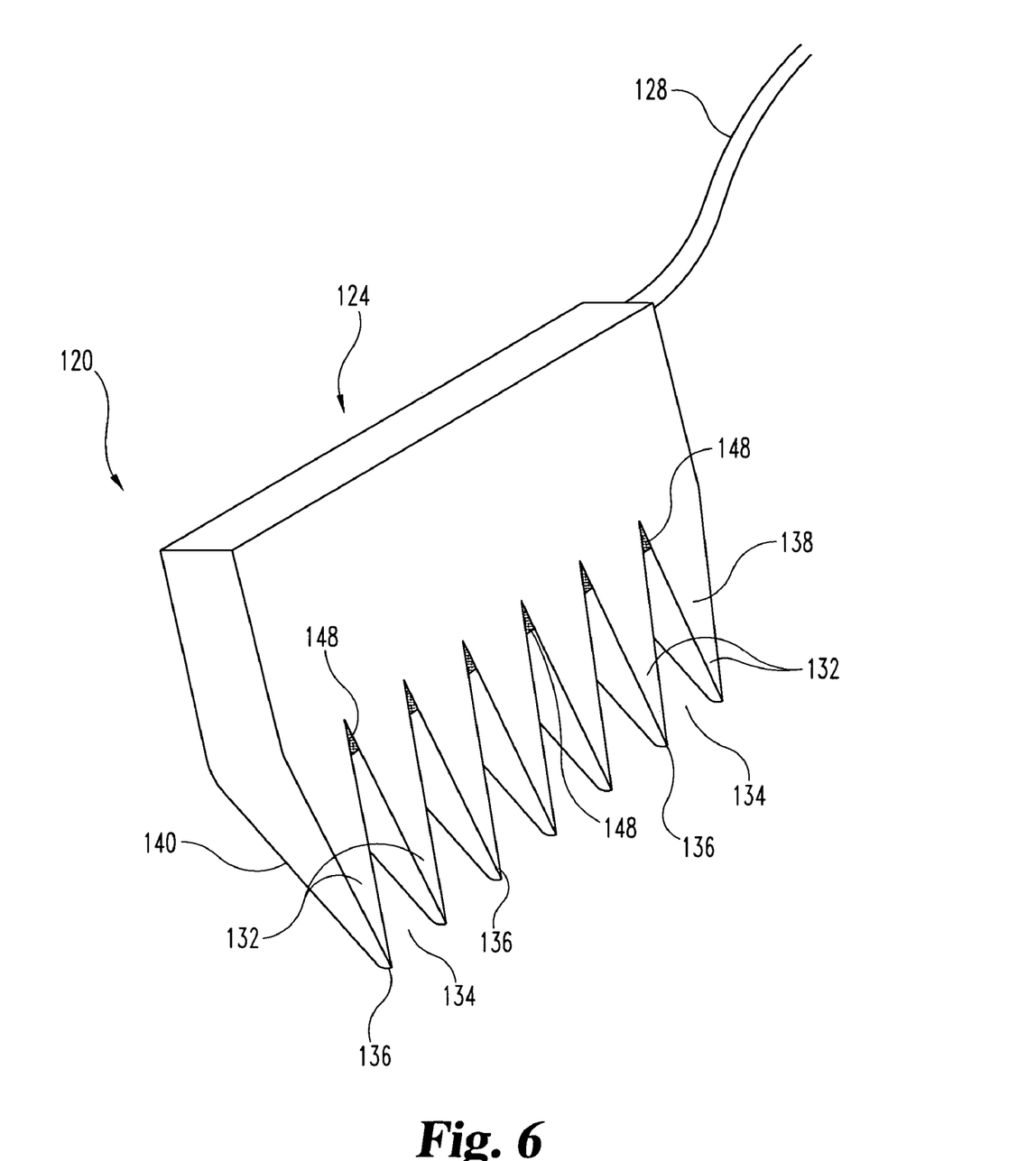
FIG. 6 is a perspective view of an embodiment of an instrument according to the present disclosure that can used for surgical dissection of various tissues.

As indicated above, the illustrated embodiment of instrument 20 could be used, for example, with a relatively square implant or one with a convex leading edge. Other configurations for an instrument according to the principles herein are also possible. For example, as seen in FIG. 6, a long and narrow instrument 120 for dissection and hemostasis, for example of solid organs such as the liver or spleen, can be provided in accordance with those principles. Instrument 120 generally includes an operating portion 124, which can be held by the surgeon's hand or a gripping tool, or may be provided with a handle such as handle 22 or 22' discussed above. Operating portion 124 has a set of projections 132 separated by a set of gaps 134. Projections 132 have sharp tips 136 and opposing surfaces 138 and 140, which are essentially the same as tips 36 and surfaces 38 and 40 described above. Wire or cable 128 is connected to a power source (not shown) and to an cauterization element 148, which passes through projections 132 and gaps 134, substantially as discussed above with respect to element 48. In the embodiment of instrument 20 shown in FIG. 1, it is seen that element 48 is at the inmost part of gaps 34, while in the embodiment of instrument 120 shown in FIG. 6, there is space between element 148 and the inmost end of gaps 134. The placement of element 48 shown in FIG. 1 may be used in any of the instrument embodiments in this disclosure, as may the placement of element 148 shown in FIG. 6.

Figure 7A:
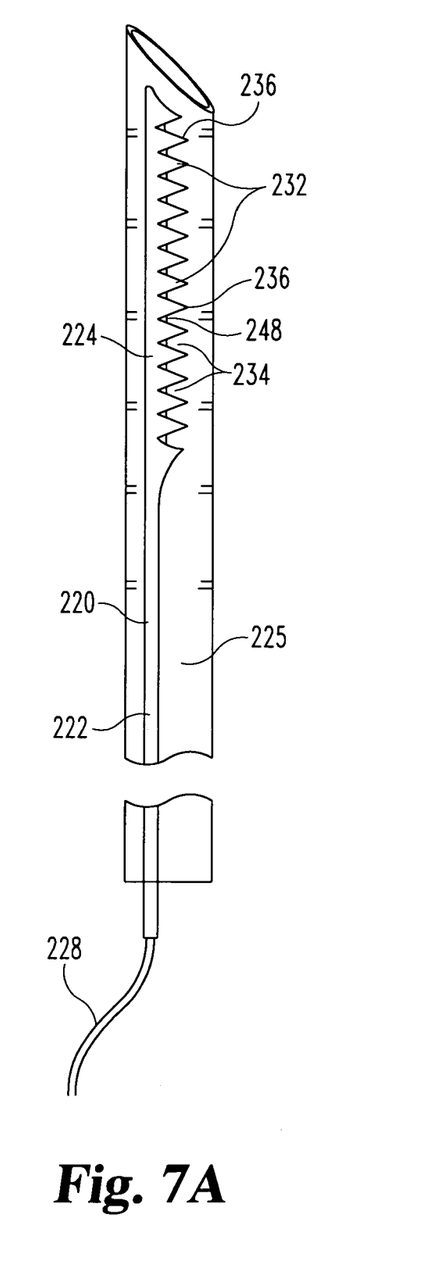
FIG. 7A is a perspective view of an embodiment of an instrument according to the present disclosure that can be delivered minimally-invasively (e.g. through a laproscopic or endoscopic port) for tissue dissection, in a non-extended state.
Figure 7B:
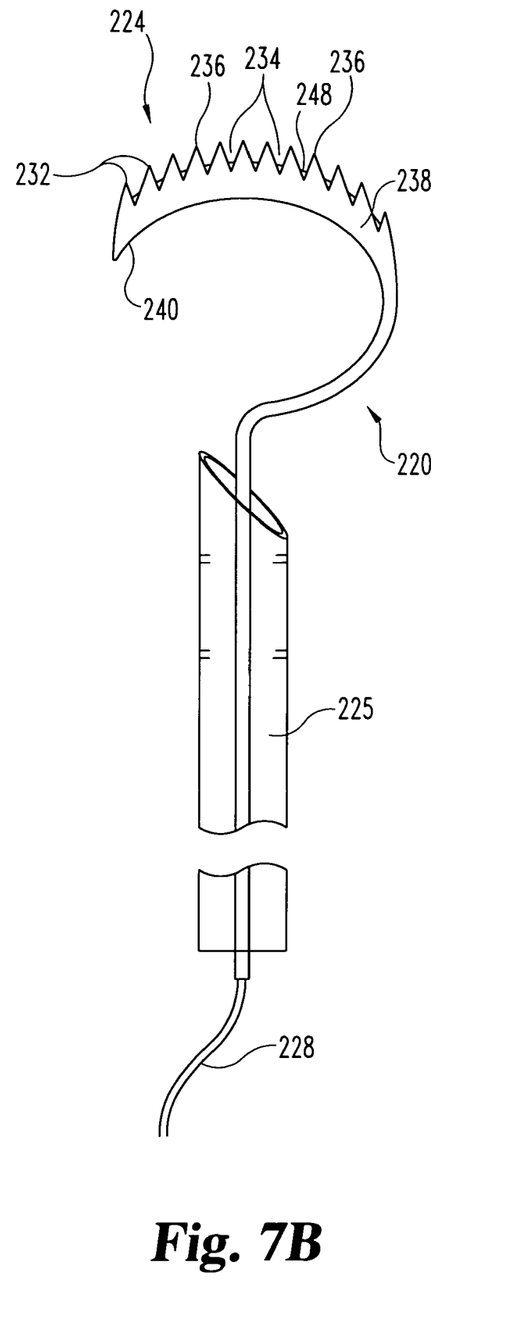
FIG. 7B is a perspective view of the embodiment of FIG. 7A in an extended state.

Another embodiment of an instrument 220 is shown in FIGS. 7A-7B. In that embodiment, instrument 220 is designed for endoscopic, laparoscopic, or other minimally-invasive use. Instrument 220 includes a handle portion 222 and an operating portion 224, which can be ejected from and retracted into a sheath or sleeve 225. Like instruments 20, 20' and 120, instrument 220 includes a wire or cable 228 for conducting electrical power, which extends through handle 222 and into operating portion 224, and operating portion 224 includes a set of projections 232 separated by a set of gaps 234. Projections 232 include sharpened tips 236 in the form of edges or points, and opposing surfaces 238 and 240 that are a part of opposing surfaces of operating end 224. A cauterization element 248 passes through projections 232 and gaps 234, which in the illustrated embodiment is substantially as shown with respect to instrument 20 in FIG. 1.

Operating portion 224 of instrument 220 is made of a substantially elastic material in this particular embodiment. Thus, when operating portion 224 is pushed out of sheath 225, it seeks to take on its generally unstressed shape, shown in one example in FIG. 7B as an arc of a circle. When operating portion 224 is placed or drawn into sheath 225, it elastically straightens. Accordingly, instrument 220 may be used by inserting sheath 225 (with instrument 220 inside) through a minimally-invasive opening such as a laparoscopic port. When the distal end of sheath 225 is at the surgical site, instrument 220 is extended from sheath 225. In the embodiment in which operating portion 224 is substantially elastic, operating portion assumes its generally unstressed shape or configuration. With operating portion 224 extended from sheath 225, it can be used to dissect tissue for placement of an implant, as generally described above, or it may be used for biopsy or other excision of tissue, or for other appropriate tissue cutting tasks that a surgeon may desire. Projections 232 and cauterization element 248 operate substantially as indicated above with respect to projections 32 and element 48, using sharp and blunt dissection with cauterization of vessels to minimize tissue damage and fluid loss.

The embodiments of instruments described herein may be made of any of a variety of suitable materials, bearing in mind the intended use in a surgical environment with a cauterization element. Thus, materials with low melting points are generally less preferable. Metals such as stainless steel, perhaps with a plastic or rubber coating for the handle, may be particularly useful because of their potential for sharpness. In embodiments such as instrument 20', operating portion 24' and cauterization element 48' and associated parts are of a long-term biocompatible material (e.g. stainless steel, titanium, certain ceramics, certain hard plastics, etc.), since they may remain in the body, as discussed above. Balloons or inflatable portions may be provided on an operating portion (e.g. portion 24) with a conduit extending through a handle portion (e.g. handle 22) for injection of gas or liquid to inflate such a balloon or portion. As one example, ridge 42 and/our mound 44, or other part(s) of upper or lower surfaces of operating portion 24, could be formed as an inflatable balloon, which provides blunt dissection. As already noted, the disclosed instruments, and especially their operating portions, may be of any shape or size, and preferably will correspond to the shape and size of the implant that is being implanted.

While the disclosure has been illustrated and described in detail in the drawings and foregoing description, the same is to be considered as illustrative and not restrictive in character, it being understood that only illustrated embodiments have been shown and described and that all changes and modifications that come within the spirit of the disclosure are desired to be protected.

What is claimed is:

1. A surgical apparatus for cutting and cauterizing tissue, comprising: a handle portion having an opening therethrough;
    an operating portion connected to said handle portion, said operating portion including a plurality of projections each having a respective sharpened tip and a base portion, said projections being separated from one another by respective gaps, said operating portion having an upper surface with a ridge adjacent said projections and a mound between said ridge and said handle portion, wherein said operating portion has a longitudinal axis generally along a direction of travel of said operating portion, wherein said mound slopes directly down to edge portions of said operating portion that are laterally offset from said longitudinal axis;
    an electrical conductor extending through said handle portion and said operating portion; and
    a cauterization element connected to said conductor, said cauterization element extending through the base portions of said projections and being exposed in said gaps, so that said tips of said projections are forward of said cauterization element.

2. The apparatus of claim 1, wherein said operating portion is of a size and shape that is substantially the same as an implant.

3. The apparatus of claim 1, wherein said cauterization element is electrically connected to said conductor.

4. The apparatus of claim 3, wherein said tips form a convex leading edge for sharp dissection.

5. The apparatus of claim 1, wherein said operating portion includes a bay for holding an implant, said bay having internal walls sized to be at least as tall as the implant.

6. The apparatus of claim 5, wherein said operating portion is detachable from said handle portion and biocompatible so that said operating portion may be included as part of an implant, said operating portion including at least one channel for anchoring one or more sutures.

7. The apparatus of claim 1, wherein said operating portion is narrow and planar, and said projections form one side of said operating portion.

8. The apparatus of claim 1, and said ridge is non-parallel to said axis of the apparatus.

9. The apparatus of claim 8, wherein said ridge extends in a curve that defines an arc that crosses said axis, said arc being concave facing said mound.

10. The apparatus of claim 9, wherein said tips'of said projections extend in a curve, and the curve of the ridge is substantially the same as the curve of the projections.

11. The apparatus of claim 8, wherein said ridge is entirely behind said sharpened tips.

12. The apparatus of claim 9, wherein said curve of said ridge is substantially in a plane, said plane being substantially parallel to said upper surface of said operating portion.

13. The apparatus of claim 1, wherein said operating portion has a bottom surface opposite the mound which is at least partly convexly curved, said convex curve extending beyond said mound toward said handle portion.

14. The apparatus of claim 1, wherein said mound has a round upper surface from which concave sides extend that curve into edges of the operating portion.

15. The apparatus of claim 14, wherein said mound upper surface is substantially circular in a plane substantially parallel to said upper surface of said operating portion.

16. The apparatus of claim 15, wherein said mound has a middle point substantially in the center of said circular upper surface of said mound that has a constant height above said projections.

17. The apparatus of claim 14, wherein said upper surface of said mound has concave sides that curve into both lateral edges of the operating portion.

18. The apparatus of claim 14 wherein said upper surface of said mound has concave sides that curve directly into edges of said operating portion.

19. The apparatus of claim 1, wherein said mound is placed entirely behind said ridge, said mound being greater in height than said ridge.

20. The apparatus of claim 1, wherein said mound is a plateau-shaped mound that slopes down on all sides to lateral and longitudinal portions of said operating portion.

21. The apparatus of claim 1, wherein said ridge is substantially parallel to a curved line connecting said tips.

22. A method, comprising:
providing the apparatus of claim 1;
making an incision into a patient;
inserting at least a portion of said apparatus into the patient through the incision;
forming an open subdermal pocket with said apparatus; and
inserting an implant into said pocket.

23. A surgical apparatus for cutting and cauterizing tissue, comprising:
a handle portion having an opening therethrough; an operating portion connected to said handle portion, said operating portion including a plurality of projections each having a respective sharpened tip and a base portion, said projections being separated from one another by respective gaps, said operating portion having an upper surface with a ridge adjacent said projections and a mound between said ridge and said handle portion, wherein said operating portion has a longitudinal axis generally along a direction of travel of said operating portion, wherein said mound slopes directly down to edge portions of said operating portion that are laterally offset from said longitudinal axis;
an electrical conductor extending through said handle portion and said operating portion; and
a cauterization element connected to said conductor, said cauterization element extending through said projections and being exposed in said gaps, wherein said tips of said projections are separate from said cauterization element.

* * * * *